US011331434B2

(12) United States Patent
Vogt

(10) Patent No.: US 11,331,434 B2
(45) Date of Patent: May 17, 2022

(54) BOTULINUM TOXIN PREFILLED SYRINGE SYSTEM

(71) Applicant: Merz Pharma GmbH & Co. KGAA, Frankfurt am Main (DE)

(72) Inventor: Markus Vogt, Frankfurt am Main (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 102 days.

(21) Appl. No.: 16/311,728

(22) PCT Filed: Jun. 20, 2017

(86) PCT No.: PCT/EP2017/065050
§ 371 (c)(1),
(2) Date: Dec. 20, 2018

(87) PCT Pub. No.: WO2017/220553
PCT Pub. Date: Dec. 28, 2017

(65) Prior Publication Data
US 2019/0201630 A1     Jul. 4, 2019

(30) Foreign Application Priority Data
Jun. 22, 2016 (EP) ..................... 16001404

(51) Int. Cl.
*A61M 5/31* (2006.01)
*A61M 5/315* (2006.01)
(Continued)

(52) U.S. Cl.
CPC ..... *A61M 5/31513* (2013.01); *A61K 38/4893* (2013.01); *A61M 5/178* (2013.01);
(Continued)

(58) Field of Classification Search
CPC ............ A61M 5/31513; A61M 5/3158; A61M 5/3202; A61M 5/488; A61M 5/002;
(Continued)

(56) References Cited

U.S. PATENT DOCUMENTS 4,303,070 A * 12/1981 Ichikawa .......... A61M 5/31513
604/222
5,597,530 A *  1/1997 Smith ...................... A61L 2/07
134/150

(Continued)

FOREIGN PATENT DOCUMENTS

CN      101249291 A     8/2008
CN      103930595 A     7/2014
(Continued)

OTHER PUBLICATIONS

PCT International Search Report for PCT/EP2017/065050, dated Aug. 14, 2017.
(Continued)

*Primary Examiner* — Amber R Stiles
(74) *Attorney, Agent, or Firm* — McBee Moore & Vanik IP, LLC

(57) ABSTRACT

The present invention relates a botulinum toxin prefilled syringe system with desirable injection force characteristics, in particular low gliding force and low break loose force, comprising a syringe barrel of glass containing a liquid botulinum toxin composition, a plunger stopper and a closure device such as a tip cap or a needle shield. In addition, the present invention relates to a kit comprising the botulinum toxin prefilled syringe system, and optionally instructions for use, and to the use of the botulinum toxin prefilled syringe system in therapeutic and cosmetic applications.

20 Claims, 5 Drawing Sheets

(51) Int. Cl.
- *A61M 5/48* (2006.01)
- *A61M 5/178* (2006.01)
- *A61K 38/48* (2006.01)
- *A61M 5/32* (2006.01)
- *A61M 5/00* (2006.01)

(52) U.S. Cl.
CPC .......... *A61M 5/3158* (2013.01); *A61M 5/488* (2013.01); *A61M 5/002* (2013.01); *A61M 5/3202* (2013.01); *A61M 2005/312* (2013.01); *A61M 2005/3151* (2013.01); *A61M 2202/049* (2013.01); *A61M 2202/07* (2013.01); *A61M 2205/0222* (2013.01); *A61M 2205/0238* (2013.01)

(58) Field of Classification Search
CPC .... A61M 2005/312; A61M 2005/3151; A61M 2202/07; A61M 2202/049; A61M 2205/0222; A61M 2205/0238; A61M 5/178; A61M 5/281; A61M 5/285; A61M 2005/3126; A61M 2005/3104; A61M 5/315; A61M 5/31511; A61M 2005/31521; A61K 38/4893

See application file for complete search history.

(56) References Cited

U.S. PATENT DOCUMENTS

| | | | |
|---|---|---|---|
| 2005/0010175 A1* | 1/2005 | Beedon | A61M 5/31511 604/218 |
| 2011/0252899 A1 | 10/2011 | Felts et al. | |
| 2015/0297800 A1* | 10/2015 | Weikart | A61M 5/3129 600/432 |
| 2016/0243305 A1 | 8/2016 | Nakamura et al. | |

FOREIGN PATENT DOCUMENTS

| | | |
|---|---|---|
| CN | 104350134 A | 2/2015 |
| CN | 104759005 A | 7/2015 |
| CN | 104841043 A | 8/2015 |
| EP | 2910265 A1 | 8/2015 |
| JP | 2007195742 A | 8/2007 |
| TW | 201637641 A | 11/2016 |
| WO | 2008/064283 A2 | 5/2008 |
| WO | 2013/178647 A1 | 12/2013 |
| WO | 2014/085346 A1 | 6/2014 |
| WO | 2015/064299 A1 | 5/2015 |
| WO | 2015065942 A1 | 5/2015 |
| WO | 2016/039816 A1 | 3/2016 |

OTHER PUBLICATIONS

International Organization for Standardization, "Sterile hypodermic syringes for single use—Part 1: Syringes for manual use," (1993).

* cited by examiner

BOTULINUM TOXIN PREFILLED SYRINGE SYSTEM

CROSS-REFERENCE TO RELATED APPLICATIONS

This application is a National Stage entry of International Application No. PCT/EP2017/065050, filed Jun. 20, 2017, which claims priority to European Patent Application No. 16001404.9, filed Jun. 22, 2016.

BACKGROUND

Field of the Invention

The present invention relates a botulinum toxin prefilled syringe system with desirable injection force characteristics, in particular low gliding force and low break loose force, comprising a syringe barrel of glass containing a liquid botulinum toxin composition, a plunger stopper and a closure device such as a tip cap or a needle shield. In addition, the present invention relates to a kit comprising the botulinum toxin prefilled syringe system, and optionally instructions for use, and to the use of the botulinum toxin prefilled syringe system in therapeutic and cosmetic applications.

Description of Related Art

Prefilled syringes (PFS) are increasingly used as a drug delivery device because of the range of compelling benefits, such as patient safety, convenience, dosing accuracy, reliability, and reduced amount of drug waste, over conventional delivery systems like vials and ampoules. Nowadays, prefilled syringes are considered to be the presentation of choice for numerous injectable drugs across a broad range of applications.

The presentation of highly sensitive biological drugs like protein-based drugs in a prefilled syringe format is, however, often a key challenge for pharmaceutical companies. One reason is that the stability of protein-based drugs is frequently limited due to their high sensitivity to pH, temperature, ionic strength, specific chemical substances (e.g., free silicone particles) and other factors. Protein-based drugs also generally have a high tendency to adsorb on syringe surfaces and are prone to aggregation and denaturation. Furthermore, the interaction of the liquid protein formulation with the syringe materials during storage generally leads to the release of substances (so-called "extractables" and "leachables") which have the potential to exert an adverse effect on protein stability and activity.

Another major concern for developers of prefilled syringes for highly sensitive protein-based drugs is the syringe functionality over time. For example, the sliding force may be too high to ensure the desired convenience, precision and accuracy of injection. Furthermore, the break loose force, especially after long-term storage of the prefilled syringe, may be inacceptable high leading to the risk of overdosing. It is therefore essential that the plunger moves freely when required to do so, and does not become stuck to the barrel even after long-time storage. However, syringe materials that might provide the desired syringe functionality, are frequently incompatible with sensitive protein-based drugs because of the release of extractables/leachables and other substances that may destabilize protein-based drugs. Therefore, it is in many cases a major challenge to obtain the desired syringe functionality.

Botulinum toxin is an example of the above-mentioned sensitive protein-based drugs. It is a highly potent neurotoxin and is produced by *Clostridium botulinum* and related *Clostridium* spp. Today, it is used in the treatment of a wide range of debilitating neuromuscular diseases (e.g., cervical dystonia, blepharospasm, spasticity, and hyperhidrosis) as well as in aesthetic medicine (e.g., treatment of facial wrinkles). The active principle of botulinum toxin, which naturally exists as a complex with other non-toxic clostridial proteins, is the neurotoxic polypeptide (also referred to as the "neurotoxic component"). The neurotoxic component exists in different serotypes (serotypes A to G) and consists of a heavy chain of about 100 kDa and a light chain of about 50 kDa.

Due to its inherent instability, botulinum toxin is commonly marketed as a lyophilized formulation for reconstitution with physiological saline prior to use, such as Botox® (Allergan Inc., Irvine, Calif.), Dysport® (Ipsen, France), and Xeomin® (Merz Pharma GmbH & Co. KGaA, Germany). The use of such lyophilized products, however, suffers from a number of drawbacks like inconvenience of use, sterility issues, inaccurate dosing, solubilizing/dilution problems, wasting of expensive reconstituted toxin, and limited storage time of the toxin formulation after reconstitution.

Therefore, there is a strong demand in the art for a botulinum toxin prefilled syringe which provides sufficient toxin stability but also has the desired functionality in terms of suitable injection force characteristics. In particular, there is a great interest in a botulinum toxin syringe having a low gliding force to allow accurate administration of a given dose, even if low amounts of toxin are to be injected and/or the toxin is to be administered by multiple injections. Furthermore, there is also a great interest in a botulinum toxin syringe having a low break loose force to allow for repeated precise toxin injection and to mitigate the risk of toxin overdosing.

SUMMARY

In view of the above, the objective of the present invention is to provide a stable botulinum toxin prefilled syringe having excellent functionality in terms of injection force characteristics.

The above object is solved by the provision of a botulinum toxin prefilled syringe system, which not only exhibits a sufficient stability of the botulinum toxin inside the syringe but also exhibits a favorably low gliding force and break loose force, respectively. It was found that the beneficial chemical and mechanical properties of the botulinum toxin prefilled syringe system can also be achieved upon long-term storage and, thus, over its entire shelf-life. The prefilled syringe system of the present invention therefore represents a convenient, reliable and safe way of botulinum toxin administration.

In a first aspect, the present invention provides a botulinum toxin prefilled syringe system comprising:

- a syringe barrel of glass, the syringe barrel including an inner surface defining a chamber containing a liquid botulinum toxin formulation, having a proximal end and a distal end, and optionally having a label attached to its outside surface;
- a plunger stopper slidably positioned inside the syringe barrel and providing a fluid-tight seal of the proximal end of the syringe barrel;
- a closure device attached to the distal end of the syringe barrel, the closure device having an outlet engaging portion sealingly engaging and closing a distal open outlet end of the syringe system to prevent leakage of the liquid botulinum toxin formulation;

characterized in that the botulinum toxin prefilled syringe system has a normalized maximum gliding force of 20 N or less, as measured at a temperature of 20° C. using a 32 G×½" needle and a displacement speed of 100 mm/min, wherein the normalized maximum gliding force is defined as follows:

$$GF_{max} = GF_{measured} \times (d_{barrel})^2 / (D_{barrel})^2$$

wherein:

$GF_{max}$ is the normalized maximal gliding force in N, $GF_{measured}$ is the measured highest gliding force in N before the plunger stopper finishes its course at the distal end of the syringe barrel, $d_{barrel}$ is the barrel inner diameter of a reference syringe and is 6.35 mm, and $D_{barrel}$ is the inner barrel diameter in mm of the prefilled syringe system.

In addition, the botulinum toxin prefilled syringe system preferably exhibits no or only a small break loose force peak (break loose force is the force required to initiate the movement of the plunger). This is, there is no or essentially no force peak for overcoming the resistance between the plunger stopper and the inside surface of the syringe barrel, and no sharp decline at the transition from break loose to gliding force. Rather, in a recorded force vs. displacement plot, the break loose force may directly merge into the increase of gliding force. Moreover, the botulinum toxin prefilled syringe system further preferably has a low dynamic gliding force (the force required to sustain the movement of the plunger to expel the content of the syringe).

In a second aspect, the present invention provides a kit comprising a botulinum toxin prefilled syringe system according to the first aspect of the invention and optionally instructions for use of said botulinum toxin prefilled syringe system.

In a third aspect, the present invention provides a botulinum toxin prefilled syringe system according to the first aspect of the invention for use in therapy. Preferably, the botulinum toxin prefilled syringe system is used for treating a disease or condition caused by or associated with hyperactive cholinergic innervation of muscles or exocrine glands in a patient including, but not limited to, dystonia, spasticity, paratonia, diskinesia, focal spasm, strabismus, tremor, tics, migraine, sialorrhea and hyperhidrosis.

In a fourth aspect, the present invention relates to the use of the botulinum toxin prefilled syringe system according to the first aspect of the invention in cosmetic applications, particularly for cosmetic treatment of wrinkles of the skin and facial asymmetries, e.g. for the treatment of glabellar frown line, crow's feet, upper facial rhytides and platysma bands.

In a fifth aspect, the present invention provides a method for treating a disease or condition caused by or associated with hyperactive cholinergic innervation of muscles or exocrine glands in a patient, the method comprising locally administering an effective amount of botulinum toxin to a muscle or exocrine gland of the patient using the botulinum toxin prefilled syringe system according to the first aspect of the invention.

In a sixth aspect, the present invention provides a method for the cosmetic treatment of the skin, particularly for treating wrinkles of the skin and facial asymmetries, the method comprising locally administering an effective amount of botulinum toxin to a patient by injection, preferably by intradermal, subdermal or subcutaneous injection, using the botulinum toxin prefilled syringe system according to the first aspect of the present invention.

Further embodiments of the present invention are set forth in the appended dependent claims, and these and other embodiments of the present invention will be more fully understood by reference to the following detailed description of the invention, the examples and the accompanying drawings.

BRIEF DESCRIPTION OF THE DRAWINGS

The following detailed description of the invention will be best understood in conjunction with the accompanying drawings in which.

DETAILED DESCRIPTION OF A PREFERRED EMBODIMENT

Figure 1:
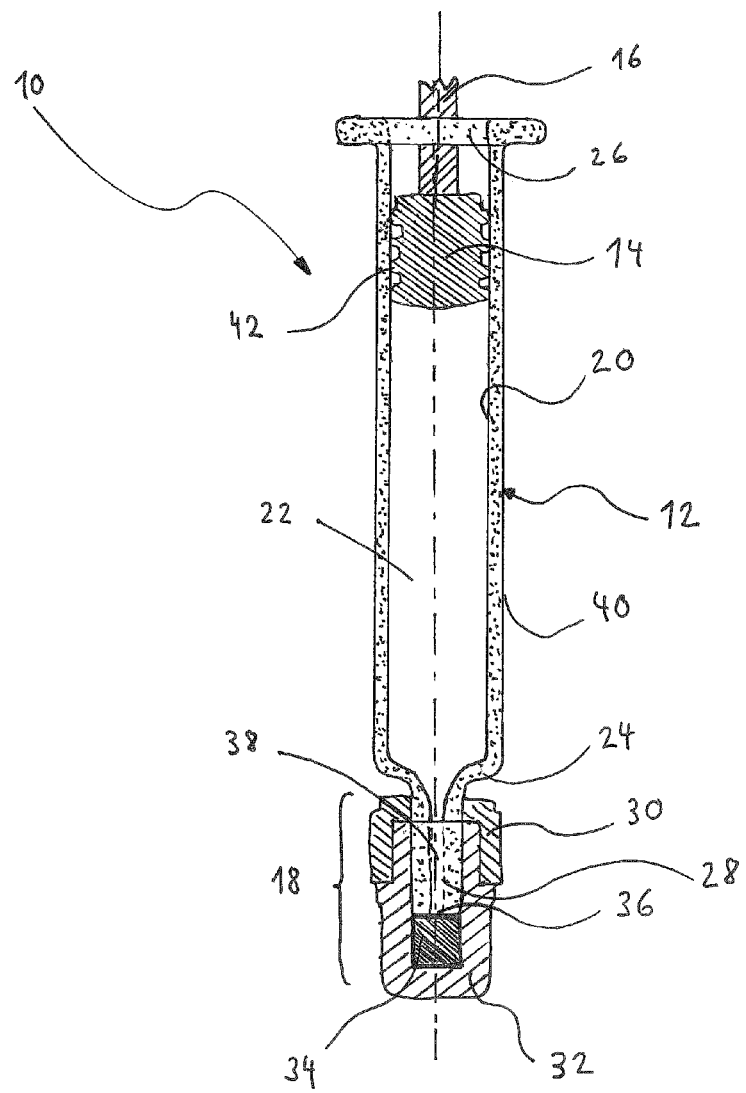
FIG. 1 is a cross-sectional side elevation view of an exemplary prefilled syringe system of the present invention.

The present invention provides a botulinum toxin prefilled syringe system providing the desired protein stability and having excellent functionality in terms of injection characteristics. More specifically, despite the complex and labile nature of botulinum toxin and its highly diluted use, the prefilled syringe system of the present invention provides a long sought solution to the technical challenges of protein stability and syringe functionality (break loose, glide force, etc.).

Advantageously, the botulinum toxin prefilled syringe system of the present invention has a gliding force that allows for smooth sliding of the plunger stopper inside the syringe barrel over the entire plunger displacement distance. This enables the operator to completely discharge of all content of the syringe in a convenient and accurate manner and to avoid wasting of expensive toxin material. The gliding force is, however, also not too low so as to result in an undesirable dripping of the highly neurotoxic liquid botulinum toxin formulation on, for example, the patient's skin after stopping the injection or during change of the injection site.

In addition, the break loose force, i.e. the force required to initiate the movement of the plunger stopper, of the botulinum toxin prefilled syringe system of the present invention is favorably low. A too high break loose force, especially in combination with a sharp decline at the transition from break loose to gliding force is known to cause problems to the syringe user like overdosing of the drug to be administered. This is particularly important if the content of the drug formulation in the prefilled syringe is to be applied by multiple puncture techniques, which is typically the case for botulinum toxin.

Surprisingly, the above mentioned beneficial properties of the prefilled syringe system of the present invention can be attained over the entire shelf-life of a prefilled syringe, e.g. after storage for 12 months. This is, potential undesirable changes typically occurring after several months of storage as encountered for other prefilled syringe formats, e.g. increased gliding force and/or increased break loose force (e.g., because the plunger stopper gets stuck) after several months of storage, are essentially not observed for the prefilled syringe system of the present invention. In fact, even long-term storage of the botulinum toxin syringe of the present invention for no less than 18 to 24 months was, surprisingly, found to not lead to a significant deterioration of its beneficial properties.

Thus, due to the many advantages associated with the prefilled syringe type presentation of drugs, including minimized dosing errors, enhanced safety, high convenience and ease of use as well as reduced costs due to minimized loss or waste of toxin, the botulinum toxin prefilled syringe of the present invention is expected to represent a win-win solution for end-uses as well as manufacturers and to have a great potential.

In the following, some aspects and features of the botulinum toxin prefilled syringe system of the present invention will be described with reference to the accompanying drawings which, however, are to be considered as exemplifications of the principle of the invention and are not intended to limit any broad aspects or generic features of the invention to the particular embodiments illustrated.

In a first aspect, the present invention relates to a botulinum toxin prefilled syringe system.

As used herein, the term "prefilled syringe" refers to a syringe which is filled with a drug composition prior to distribution to the end user. A prefilled syringe commonly includes a drug containment container forming part of a syringe body (i.e. a syringe barrel), a plunger stopper (and usually a plunger rod) to seal one open end of the syringe and for expelling the drug, and a closure device (e.g., a tip cap or a needle shield) on the outlet end of the syringe (e.g., the open end of the syringe tip or of a pre-mounted needle or cannula) to seal the distal outlet opening. The term "prefilled glass syringe", when used herein, refers to a prefilled syringe, of which at least the barrel is made of glass.

Within the present invention, the prefilled syringe system is preferably a Luer-type of syringe or syringe system, e.g., a Luer Slip or a Luer Lock syringe that may be equipped with a tip cap (if no needle is pre-mounted) or a needle shield (if a needle is pre-mounted). It is generally sterile and, thus, ready-to-use. Further, the prefilled syringe system described herein is usually intended for single use and intended to be disposable. Suitable methods for sterilization of the (empty) prefilled syringe system or components thereof include, but are not limited to, gamma radiation, ethylene oxide (ETO) treatment and moist heat (e.g., autoclaving).

The configuration of the prefilled syringe is not particularly limited and commonly comprises a fluid-receiving barrel that is removably capped by a closure device to sealingly close the distal end of the syringe, and, after filling, is closed at the proximal end by its plunger or any other means that is in fluid-tight engagement with the inner wall of the barrel. The "closure device" may, for example, be a "cap" or "tip cap" that is removed and replaced by a needle prior to use, or a sealing means like a needle shield in case of a syringe with a removable or permanent needle. To use the prefilled syringe, the tip cap, needle shield or other type of closure device are removed, optionally a needle is attached (if not already present), and the plunger tip or piston is advanced in the barrel to inject the contents of the barrel.

Referring now to FIG. 1, the prefilled syringe system 10 comprises a syringe barrel 12, a plunger stopper 14 that is usually attached to a plunger rod 16, and a closure device 18 (including, e.g., a tip cap or a needle shield). The syringe barrel 12 is made of glass and includes an inner surface 20 defining a chamber 22, and has a distal end 24 and an open proximal end 26. The wall extending between the distal end 24 and the proximal end 26 of the syringe barrel 12 may have a generally cylindrical form. The syringe generally has a syringe tip 28 distally projecting from the distal end 24 of the syringe barrel 12. The tip 28 has a fluid passage 38 extending therethrough and communicating with the barrel lumen. Alternatively, the distal end 24 of the syringe barrel 12 may be adapted for receiving a needle assembly or the like.

The plunger stopper 14 is slidably positioned inside the syringe barrel 12 and provides a fluid-tight seal of the proximal end 26 of the syringe barrel 12. The plunger stopper 14 has a plurality of annular ribs 42 providing multiple contact areas with the inner surface of the syringe barrel 12. The closure device 18 (including, e.g., tip cap or needle shield) is attached to the distal end 24 of the syringe barrel 12, usually to the tip 28, and provides a seal to prevent leakage of the liquid botulinum toxin formulation. Alternatively, a needle assembly comprising at least a needle and a needle shield is attached to the distal end 24 of the syringe barrel 12 adapted for receiving the needle assembly or the like. In a preferred embodiment, the closure device 18 is a tamper evident Luer Lock Closure (TELC), comprising a Luer Lock adaptor 30, a tamper evident elastomer part 32, and an elastomeric rubber insert 34 which sealingly engages and closes the distal open end 36 of the prefilled syringe system 10.

Furthermore, the syringe barrel 12 may have a label (not shown) attached to its outer surface 40. The label may be fixed to the outer surface 40 by an adhesive or any other suitable means, and its position on the outer surface of the syringe barrel 12 is not specifically limited. For example, the label may be positioned circumferentially around the syringe barrel 12, particularly in the upper proximal half of the syringe barrel 12. Also, the label may be a transparent label, or a label having a transparent part, with graduation marks printed or otherwise applied to the transparent label, or the transparent part. This type of label may be attached to the outer surface 40 of syringe barrel 12 in the axial direction of the syringe barrel 12.

In accordance with the present invention, the botulinum toxin prefilled syringe system is characterized in that it has a normalized maximum gliding force ($GF_{max}$) of 20 N or less, as measured using a 32 G×½" needle and a displacement speed of 100 mm/min at a temperature of 20° C., wherein the normalized maximum gliding force is defined as follows:

$$GF_{max} = GF_{measured} \times (d_{barrel})^2 / (D_{barrel})^2$$

wherein:

$GF_{max}$ is the normalized maximal gliding force in N, $GF_{measured}$ is the measured highest gliding force in N before the plunger stopper finishes its course at the distal end of the syringe barrel, $d_{barrel}$ is the barrel inner diameter of a reference syringe and is 6.35 mm, and $D_{barrel}$ is the inner barrel diameter in mm of the prefilled syringe system.

The "highest gliding force before the plunger stopper finishes its course at the distal end of the syringe barrel" within the meaning of the present invention is intended to mean the maximum force seen in a gliding force versus plunger displacement plot excluding the portion of the plot in which the force rapidly increases because of the compression of the syringe plunger against the end of the syringe body. Typically, the maximum gliding force is observed towards the end of the available plunger displacement distance, before the rapid terminal increase due to the compression of the plunger against the end of the syringe body.

Preferably, the normalized maximum gliding force $GF_{max}$ is equal to or less than 18 or 15 N, more preferably equal to or less than 12 or 10 N, and most preferably equal to or less than 8 or 7 N. However, normalized maximum gliding forces that are excessively low, e.g. below 2 N or below 1 N, are not desirable since this is expected to result in an unwanted after-sliding of the plunger after the syringe user has decided to stop injection. Further, a too low gliding force is also undesirable because this may result in the risk of unwanted dripping of the highly neurotoxic liquid botulinum toxin formulation.

Another preferable characteristic of the botulinum toxin prefilled syringe system of the present invention is that it show no or only a small break loose force peak, which is frequently observed with other prefilled syringe systems. As used herein, the term "break loose force" is intended to mean the force required to initiate the movement of the plunger or plunger stopper.

Within the context of the present invention, the normalized break loose force of the botulinum toxin prefilled syringe system of the invention is preferably 15 N or less, and preferably lower than the maximum gliding force, as measured using a 32 G×½" needle and a displacement speed of 100 mm/min at a temperature of 20° C., wherein the normalized break loose force is defined as follows:

$$BLF_{norm} = BLF_{measured} \times (d_{barrel})^2 / (D_{barrel})^2$$

wherein:

$BLF_{norm}$ is the normalized break loose force in N, $BLF_{measured}$ is the measured break loose force in N and is defined as the highest gliding force between 0 and 2 mm plunger displacement distance, $d_{barrel}$ is the barrel inner diameter of a reference syringe and is 6.35 mm, and $D_{barrel}$ is the inner barrel diameter in mm of the prefilled syringe system.

Preferably, the normalized break loose force is equal to or less than 10, 8 or 6 N, more preferably equal to or less than 5, 4 or 3 N. In addition, or separately thereof, the normalized break loose force is preferably lower than the normalized maximum gliding force ($GF_{max}$), more preferably not more than 70%, 60% or 50% of $GF_{max}$, and most preferably not more than 40%, 30% or 20% of $GF_{max}$.

Moreover, the botulinum toxin prefilled syringe system of the present invention also generally has a favorably low dynamic gliding force. As used herein, the term "dynamic gliding force" is intended to refer to the force required to sustain the movement of the plunger to expel the content of the syringe.

Within the framework of the present invention, the dynamic gliding force of the botulinum toxin prefilled syringe system is preferably 15 N or less, as measured using a 32 G×½" needle and a displacement speed of 100 mm/min at a temperature of 20° C., wherein the normalized dynamic gliding force is defined as follows:

$$DGF_{norm} = DGF_{measured} \times (d_{barrel})^2 / (D_{barrel})^2$$

wherein:

$DGF_{norm}$ is the normalized dynamic gliding force in N, $DGF_{measured}$ is the mean gliding force calculated from the measured gliding forces at ⅓ and ⅔ of the total plunger displacement distance in N, $d_{barrel}$ is the barrel inner diameter of a reference syringe and is 6.35 mm, and $D_{barrel}$ is the inner barrel diameter in mm of the prefilled syringe system.

Preferably, the normalized dynamic gliding force ($DGF_{norm}$) is equal to or less than 13, 12, 11 or 10 N, more preferably equal to or less than 8, 6 or 5 N.

In accordance with the present invention, the above indicated maximum values for the normalized maximum gliding force ($GF_{max}$), the normalized break loose force ($BLF_{norm}$), and the normalized dynamic gliding force ($DGF_{norm}$) is attained over the entire shelf-life of the prefilled syringe system of the present invention. This is, within the present invention, the normalized maximum gliding force ($GF_{max}$) may be determined without storage (i.e. immediately or shortly after preparation of the test syringe, e.g. within one week or 1-2 days of storage at 2-8° C. or 25° C.), or after storage for 12 months at 2-8° C. or 25° C., or after storage for 24 months at 2-8° C. or 25° C.

Likewise, in accordance with the present invention, the normalized maximum break loose force ($BLF_{norm}$) may be determined without storage (i.e. immediately or shortly after preparation of the test syringe, e.g. within one week or 1-2 days of storage at 2-8° C. or 25° C.), or after storage for 12 months at 2-8° C. or 25° C., or after storage for 24 months at 2-8° C. or 25° C. Also, the normalized dynamic gliding force ($DGF_{norm}$) may be determined without storage (i.e. immediately or shortly after preparation of the test syringe, e.g. within one week or 1-2 days of storage at 2-8° C. or 25° C.), or after storage for 12 months at 2-8° C. or 25° C., or after storage for 24 months at 2-8° C. or 25° C.

Furthermore, for the sake of completeness, it should be noted that the measurements described herein to determine the gliding force, including the maximum gliding force, the break loose force, the dynamic gliding force and so on are carried out using prefilled syringe system containing the liquid botulinum toxin formulation. In other words, the botulinum toxin prefilled syringe system is not emptied and then measured ("empty syringe measurements").

Within the present invention, the plunger stopper of the botulinum toxin prefilled syringe system of the invention preferably has a plurality of annular ribs, particularly two to six, more particularly two to five or three to four, and most particularly three annular ribs.

Figure 2:
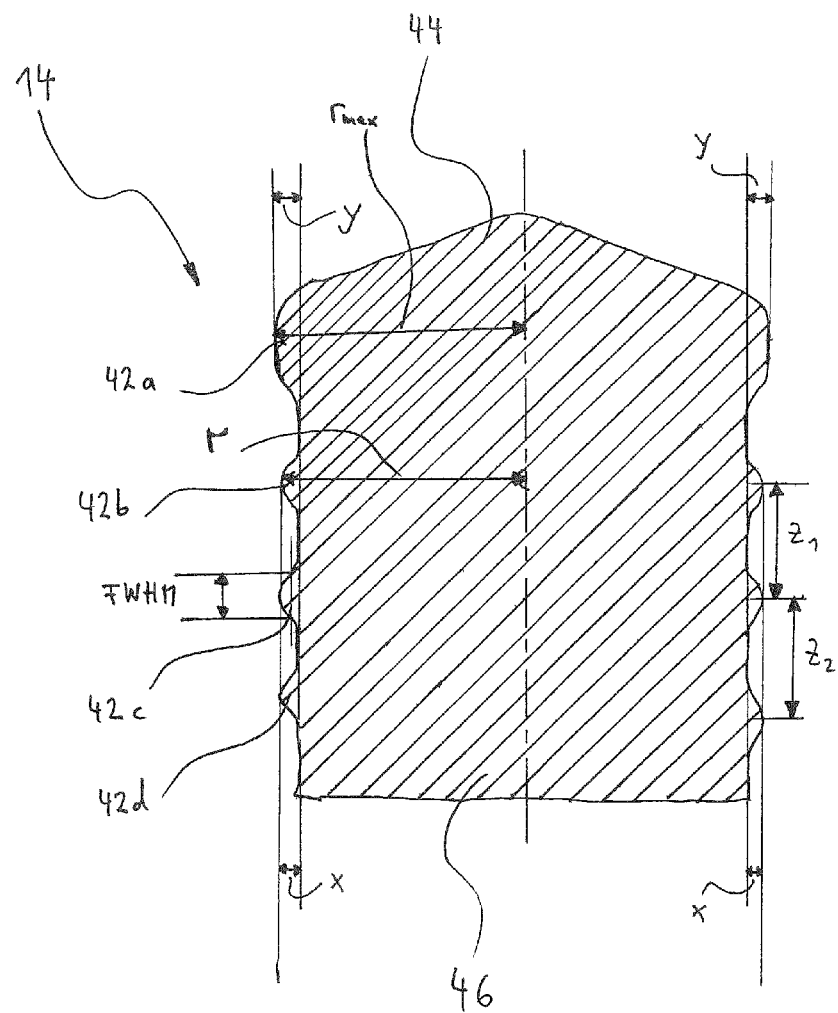
FIG. 2 is a cross-sectional side elevation view of an exemplary plunger stopper of the prefilled syringe system of the present invention.

Referring now to FIG. 2, the annular ribs 42a, 42b, 42c and 42d of the plunger stopper 14 provide multiple discrete contact areas of the plunger stopper 14 to engage with the inner surface 20 of the syringe barrel 12. The annular ribs may also referred to as "annular lobs" or "lamella" and generally extend radially outward from the axis of the plunger stopper. Each discrete contact area between the plunger stopper 14 and the inner surface 20 of the syringe barrel 12 provides an independent seal to meet the required container closure integrity (CCI) to maintain the sterility and product quality of the sterile botulinum toxin formulation product inside the chamber of the prefilled syringe.

Within the framework of the present invention, the term "annular rib" is not limited to a particular shape or geometry. For example, annular ribs 42b, 42c and 42d roughly have the shape of laterally protruding, optionally flattened, microspheres when viewed in a cross-sectional side elevation view. In contrast, annular rib 42a is, for example, a circumferential protrusion with a large width in the proximal-distal axis direction.

The plunger stopper 14 may have an annular rib 42a located adjacent a distal end 44 of the plunger stopper 14, which has a full width at half maximum (FWHM) in the axial direction of the plunger stopper 14 which is greater than FWHM of an annular rib 42b, 42c, 42d located adjacent a proximal end 46 of the plunger stopper 14, wherein the FWHM is herein defined as the width in the axial direction of the plunger stopper 14 between those two points on the surface of an annular rib (see, e.g., annular rib 40c) which are half the maximum height (in FIG. 2 labeled "x" for annular ribs 42b, 42c and 42d, and "y" for annular rib 42a) of the annular rib (see, e.g., annular rib 40c) in perpendicular direction to the axis of the plunger stopper. Alternatively, all annular ribs of a plunger stopper 14 of the present invention may have the same FWHM, or an annular rib (see, e.g., annular rib 42d) located adjacent a proximal end 46 of the plunger stopper 14 may have a FWHM that is greater than the FWHM of an annular rib (see, e.g., 42a, 42b, 42c located adjacent a distal end 44 of the plunger stopper 14.

Generally, the distance between any two proximal adjacent annular ribs (i.e. all annular ribs except the most distal annular rib) in the axial direction of the plunger stopper is at least two times the sum of the full width at half maximum (FWHM) of the two adjacent annular ribs, wherein the full width at half maximum is defined as above. Referring to FIG. 2, said distance between any two adjacent annular ribs is shown as $z_1$ and $z_2$.

In accordance with the present invention, the plunger stopper has a normalized total contact area with the inner surface of the syringe barrel of 70 mm$^2$ or less, wherein the normalized total contact area is calculated as follows:

$$TCA_{norm} = TCA_{calc} \times (d_{barrel})^2 / (D_{barrel})^2$$

wherein:
$TCA_{norm}$ is the normalized total contact area in mm$^2$,
$TCA_{calc}$ is the calculated total contact area in mm$^2$ and is defined as the sum of the contact surfaces ($CT_{rib}$) of each annular rib in mm$^2$, wherein $CT_{rib} = 2\pi r h$, with r being the greatest distance perpendicular to the axis of the plunger stopper between a point on the surface of the annular rib and the axis of the plunger stopper in mm, and h being the full width at half maximum (FWHM) of the annular rib in mm, the FWHM being defined as the width in the axial direction of the plunger stopper between those two points on the surface of the annular rib which are half the maximum height of the annular rib in perpendicular direction to the axis of the plunger stopper,
$d_{barrel}$ is the barrel inner diameter of a reference syringe and is 6.35 mm, and
$D_{barrel}$ is the inner barrel diameter in mm of the prefilled syringe system.

Referring to FIG. 2, the distance "r" is exemplary shown for annular rib 42b as a double-headed arrow. Furthermore, the FWHM is shown as a double-headed arrow labeled "FWHM".

Preferably, the normalized total contact area ($TCA_{norm}$) is 60, 50 or 40 mm$^2$ or less, more preferably, 35 mm$^2$ or less.

Furthermore, the percentage of the calculated total contact area of the plunger stopper with the inner surface of the syringe barrel to the total side face area (TSFA) of the plunger stopper is preferably 50% or less, more preferably 40% or less, and most preferably 35% or less. The calculated total contact area ($TCA_{calc}$) is defined as set out above. The total side face area (TSFA) of the plunger stopper is defined as follows:

$$TSFA = 2\pi r_{max} H$$

wherein:
TSFA is the total side face area of the plunger stopper in mm$^2$,
$r_{max}$ is the greatest distance perpendicular to the axis of the plunger stopper between a point on the surface of any annular rib and the axis of the plunger stopper in mm, and
H is the total length of the plunger stopper in axial direction in mm.

Referring to FIG. 2, the variable "$r_{max}$" is shown as a double-headed arrow between the annular rib 42a and the axis of the plunger stopper 14. The total length of the plunger stopper (H) may be the maximum distance between a first point and a second point on the central axis of the plunger stopper in distal to proximal direction. Also, the total length of the plunger stopper (H) may be defined as the maximum length in axial direction of the plunger stopper between a first point on the surface of the proximal end of the plunger stopper and a second point on the surface of the most distal annular rib, the second point being located as distal as possible and at half the maximum height of the annular rib in perpendicular direction to the axis of the plunger stopper.

The inside surface of the glass barrel is usually coated with a lubricant layer. The lubricant layer should not only provide high lubricity, enabling the plunger to easily glide through the barrel, but also be compatible with the aqueous botulinum toxin formulation and protect its shelf life. Within the context of the present invention, the lubricant layer may be a silicone-free lubricant layer or a silicone lubricant layer.

A suitable silicone-free lubrication layer is, for example, a fluoropolymer layer (e.g., fluoropolymer (fluorocarbon) layers, such as ethylene-tetrafluoroethylene (ETFE) layers and perfluoropolyether-based (PFPE-based) layers (e.g., TriboGlide®)), as well as silicon oxide-based glass PECVD (plasma-enhanced chemical vapor deposition) coatings.

The silicone-free lubrication layer can be prepared as known in the art, for example by spraying glass syringe barrels with a perfluoropolyether oil to achieve a thin layer of lubricant on the inside surface of the syringe, followed by exposing the inner cavities to a downstream inert gas (e.g., argon or helium) plasma. The plasma treatment leads to crosslinking of the perfluoropolyether, thereby immobilizing the coating and reducing its tendency to migrate off the target surface, resulting in less particles that potentially impairs the stability/efficacy of the botulinum toxin drug. An exemplary production process is described in WO 2014/014641 A1, the content of which is incorporated herein by reference. Furthermore, a particularly suitable silicone-free barrier coating for use herein is known in the art as Tribo-Glide® coating, a perfluoropolyether coating crosslinked by plasma treatment.

A suitable silicone lubricant layer for use herein may be prepared by a siliconization method selected from, but not limited to, silicone oil-based methods (e.g., spray-on siliconization or baked-on siliconization) and vapor deposition methods (e.g., plasma enhanced chemical vapor deposition (PECVD)).

In the spray-on siliconization method, a silicone oil (e.g. DOW CORNING® 360 with a viscosity of 1000 cSt) is sprayed into the syringe (i.e. the barrel) using, e.g., a diving or static nozzle to produce a thin silicone oil layer. While silicone oil is an excellent lubricant, excess silicone oil can lead to the formation of unwanted visual and subvisual silicone oil particles. With protein-based drugs, in particular, these silicone oil particles may lead to undesirable interactions with protein drugs. For example, subvisual silicone oil particles are thought to promote protein aggregation. Therefore, since it results in fewer sub-visual and visual silicone oil particles, the baked-on siliconization processes is particularly preferred for use herein. It involves the application of silicone oil as an emulsion (e.g., DOW CORNING® 365 siliconization emulsion), which is then baked on the glass surface at a specific temperature and for a specific time.

In accordance with the present invention, the inner surface of the syringe barrel of the botulinum toxin prefilled syringe system is preferably siliconized, particularly spray-siliconized or baked-on siliconized.

The design of the syringe barrel is not particularly limited and typically has an inside diameter adjusted to accommodate the desired fill volume of, e.g., 0.5 cm$^3$, 1.0 cm$^3$, 1.5 cm$^3$ or 2.0 cm$^3$. Usually, the syringe barrel has graduated marks indicating the volume of fluid in the syringe. In addition, the syringe barrel may include a flange-style interface. The design of the flange may, for example, be compatible with ISO11040. The flange-style interface may further be compatible with an optionally present handle. Furthermore, in case of a Luer-Lock syringe, the syringe may be equipped with a Luer-Lock adaptor of, e.g., polycarbonate.

The plunger stopper is preferably of an elastomeric material and optionally has a coating on at least a portion of the plunger stopper such that the liquid botulinum toxin formulation contacts only said coating during storage and/or injection. The term "coating", as used herein, is not particularly limited and may also include a number (e.g., 1-3 or 1-2) of layers of the same or different coating compositions.

The elastomeric material of the plunger stopper is preferably a synthetic rubber selected from the group consisting of isoprene rubber, neoprene rubber, butadiene rubber, butyl rubber, styrene-butadiene copolymer, acrylonitrile-butadiene copolymer, polysulfide elastomers, urethane rubbers, and ethylene-propylene elastomers. Particularly suitable for use herein is a butyl rubber such as a halogenated butyl rubber, in particular a chloro or bromo butyl rubber. The elastomeric material may also be reinforced with an inert mineral. Further, it may be cured (e.g., with organic peroxide, phenolic resins, etc.).

Suitable coatings of the plunger stopper are generally made of a material that does not undesirably interfere with the aqueous botulinum toxin formulation and exhibits low levels of extractables/leachables. Such coatings include, but are not limited to, polypropylene, polyethylene, parylene (e.g., parylene N, parylene C and parylene HT), crosslinked silicone and, preferably, fluoropolymer coatings. Examples of suitable crosslinked silicone coatings include the B2-coating (Daikyo Seiko) or XSi™ (Becton Dickinson).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particularly, is a FluroTec® coating.

In particular, the coating of the plunger stopper is preferably a fluoropolymer coating, a crosslinked silicone coating, or a coating consisting of an outer crosslinked silicone coating layered on a fluoropolymer coating.

The "closure device" within the meaning of the present invention broadly refers to any means for closing and sealing the open outlet end of a syringe to prevent leakage. Within the present invention, the term "open outlet end" generally refers to any distal open end of a syringe that is in fluid communication with the barrel lumen. In case of prefilled syringes without pre-mounted needles, the closure device is a closure means commonly known as "tip cap". Prior to use, the tip can be removed, and a needle cannula (or needle/needle assembly) can then be securely coupled to the syringe tip.

If the prefilled syringe includes a removable or non-removable (permanent) cannula (also referred to as "needle" or "needle assembly") extending from the syringe tip for delivering the liquid botulinum toxin formulation from said syringe, the closure device may be referred to as "needle shield". Said needle shield generally has a channel with a closed end and an open end having a dimension for receiving and coupling with the cannula (needle) mounted on the tip of the syringe. Typically, the (sharpened) end of the cannula penetrates the closed end of the channel in the needle shield to seal the open end of the cannula.

The closure device (e.g., tip cap or needle shield) may be a unitary member and is usually made from a flexible and/or resilient polymeric material (e.g., an elastomer), at least a portion of which contacts and seals the distal opening of the syringe (referred to as the "outlet engaging portion"). Alternatively, the closure device may have an outer cap made of a rigid plastic material that is coupled to a flexible and/or resilient inner cap made of a flexible and resilient polymeric material (e.g., an elastomer), wherein at least a portion of the inner cap contacts and seals the distal opening of the syringe (referred to as the "outlet engaging portion").

Within the context of the present invention, the outlet engaging portion of the closure device of the botulinum toxin prefilled syringe system, e.g. of a tip cap or a needle shield, is generally of an elastomeric material optionally having a coating on an outer surface thereof such that the liquid botulinum toxin formulation contacts only said coating during storage and/or injection.

Preferably, the elastomeric material is a synthetic rubber selected from the group consisting of isoprene rubber, neoprene rubber, butadiene rubber, butyl rubber, styrene-butadiene copolymer, acrylonitrile-butadiene copolymer, polysulfide elastomers, urethane rubbers, and ethylene-propylene elastomers, and wherein the elastomeric material is preferably a styrene-butadiene copolymer, a butyl rubber or a butyl rubber-isoprene rubber blend, and said butyl rubber is preferably a halogenated butyl rubber. The elastomeric material may also be reinforced with an inert mineral. Further, it may be cured (e.g., with organic peroxide, phenolic resins, etc.).

Suitable coatings that may be optionally present on the elastomeric material are made of a material that does not undesirably interfere with the aqueous botulinum toxin formulation and exhibits low levels of extractables/leachables. A preferred example of such a coating is a coating made of a fluoropolymer, i.e. a fluorocarbon coating. Other suitable coatings for use herein include, for example, polypropylene, polyethylene, parylene (e.g., parylene N, parylene C and parylene HT), and crosslinked silicone (e.g., the B2-coating (Daikyo Seiko) or XSi™ (Becton Dickinson)).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particularly, is a FluroTec® coating.

In particular, the coating of the outlet engaging portion of the closure device is preferably a fluoropolymer coating, a crosslinked silicone coating, or a coating consisting of an outer crosslinked silicone coating layered on a fluoropolymer coating.

In accordance with the present invention, the botulinum toxin prefilled syringe system may further comprise a plunger rod. The plunger rod may be fixed to the plunger stopper by any suitable means or may be integrally formed. Preferably, the plunger rod has a first mating member which engages a second mating member of the plunger stopper to removably connect the plunger rod to the plunger stopper. The rod, like the plunger stopper, is generally designed to withstand sterilization but is not otherwise limited in any particular way. Typically, the rod is made of a plastic material such as an ethylene vinyl acetate (EVA) copolymer or a polypropylene.

The liquid botulinum toxin formulation in the prefilled syringe contains the botulinum toxin at a concentration ranging from 10 U/ml and 1000 U/ml, for example, 1 U/ml to 3000 U/ml, 10 U/ml to 1000 U/ml. Preferably, the botulinum toxin is present at a concentration of about 10 U/ml to 400 U/ml, more preferably about 25 U/ml to 200 U/ml, and most preferably about 40 U/ml to 150 U/ml (e.g., 50 U/ml, 75 U/ml or 100 U/ml).

The term "botulinum toxin", as used herein, broadly refers to any form and type of botulinum toxin. In particular, the botulinum toxin may be selected from botulinum toxin types A, B, C1, D, E, F, G, or mixtures thereof. Within the context of the present invention, the botulinum toxin is preferably of serotype A, B or C1, in particular serotype A.

Furthermore, the term "botulinum toxin", as used herein, is intended to include both the botulinum toxin complex (the "toxin complex") and the "neurotoxic component" of a botulinum toxin complex. As used herein, the term "botulinum toxin complex" or "toxin complex" refers to a high molecular weight complex comprising the neurotoxic component of approximately 150 kDa and, in addition, non-toxic proteins of *Clostridium botulinum*, including hemagglutinin and non-hemagglutinin proteins. The botulinum toxin serotype A complex is commercially available, for example, as Botox® (Allergan, Inc.) or as Dysport® (Ipsen, Ltd.).

The term "neurotoxic component", as used herein, relates to the neurotoxic polypeptide of the toxin complex (the "150 kDa" polypeptide) without any associated non-toxic proteins. The pure neurotoxic component is, for example, commercially available under the trade names Xeomin® and Bocouture® (Merz Pharmaceuticals GmbH). Within the present invention, the botulinum toxin is preferably the neurotoxic component of a botulinum toxin complex of, e.g., serotype A, B, C1, in particular of a botulinum toxin complex of serotype A. In other words, the liquid (or aqueous) botulinum toxin formulation contained in the prefilled glass syringe preferably contains (only) said neurotoxic component and is devoid of any other protein of the *Clostridium botulinum* toxin complex.

It is also contemplated that the present invention encompasses isoforms, homologs, orthologs and paralogs of botulinum toxin that show at least 50%, at least 60%, at least 70%, at least 80%, at least 90% and up to 60%, up to 70%, up to 80%, up to 90%, up to 100% sequence identity to wild-type botulinum toxin, e.g. wild-type botulinum toxin A or the neurotoxic component of botulinum toxin of serotype A1 deposited with the Gen Bank database under the accession number AAA23262. The sequence identity can be calculated by any algorithm suitable to yield reliable results, for example by using the FASTA algorithm (W. R. Pearson & D. J. Lipman PNAS (1988) 85:2444-2448). Sequence identity may be calculated by comparing two polypeptides or two domains such as two LC domains or fragments thereof.

Modified and recombinant botulinum toxins are also within the scope of the present invention. With respect to suitable mutants, reference is made to WO 2006/027207, WO 2009/015840, WO 2006/114308, WO 2007/104567, WO 2010/022979, WO 2011/000929 and WO 2013/068476, which are all incorporated by reference herein. Furthermore, the present invention also refers to botulinum toxins, which are chemically modified, e.g. by pegylation, glycosylation, sulfatation, phosphorylation or any other modification, in particular of one or more surface or solvent exposed amino acid(s). The modified, recombinant, isoforms, homologs, orthologs, paralogs and mutants suitable for use in the present invention are biologically active, i.e. able to translocate into neurons and cleave proteins of the SNARE complex (e.g., VAMP/syntaxin, synaptobrevin, and SNAP-25) to exert its acetylcholine inhibitory effects, e.g., its muscle paralyzing effects.

Within the context of the present invention, the liquid, preferably aqueous, botulinum toxin formulation may comprise various other pharmaceutically acceptable substances, for example, salts (e.g., sodium chloride), stabilizing proteins (e.g., albumin, gelatin), sugars (e.g., glucose, fructose, galactose, trehalose, sucrose and maltose), carbohydrate polymers (e.g., hyaluronic acid and polyvinylpyrollidone (PVP)), polyols (e.g. glycerol and sugar alcohols like mannitol, inositol, lactitol, isomalt, xylitol, erythritol, sorbitol), amino acids, vitamins (e.g. vitamin C), zinc, magnesium, anesthetic agents (e.g., local anesthetic agents like lidocaine), surfactants, tonicity modifiers, and the like. The term "pharmaceutically acceptable", as used herein, refers to those compounds or substances which are suitable for contact with the tissues of mammals, especially humans.

The term "comprise", as used herein, is intended to encompass both the open-ended term "include" and the closed term "consist (of)". The term "made of", as used herein, is intended to broadly relate to "produced of/from", in particular mainly produced from, and generally means "comprising" (indicating that other substances or materials may be included in some amounts). It may also mean "consisting of".

Preferably, the pH of the liquid botulinum toxin formulation in the prefilled syringe is between 5.5 to 7.8, 6.0 to 7.5, 6.5 to 7.5, 6.1 to 7.3, 6.2 to 7.2, 6.3 to 7.1, and 6.5 to 7.0 during storage. A pH within the range of 6.1 to 7.3 is advantageous in that injections of such neutral or only slightly acidic solutions are much less painful upon injection than acidic solutions.

As used herein, the term "liquid formulation" or "liquid botulinum toxin formulation" is preferably a "aqueous formulation" or "aqueous botulinum toxin formulation", which is not particularly limited and may refer to an aqueous suspension, aqueous dispersion, aqueous emulsion and is preferably an aqueous solution.

Preferably, the liquid or aqueous botulinum toxin formulation does not contain a buffer substance like a phosphate buffer, a phosphate-citrate buffer, a lactate buffer, an acetate buffer and the like. The term "buffer" as used herein denotes a pharmaceutically acceptable excipient, which stabilizes the pH of a pharmaceutical preparation. Furthermore, the liquid or aqueous botulinum toxin formulation may be free of amino acids (e.g., methionine) and/or surfactants (e.g., polysorbates such as polysorbate 80) and/or animal-derived proteins (e.g., human serum albumin (HSA) or bovine serum albumin (BSA)).

A preferred aqueous botulinum toxin formulation for use herein comprises water, botulinum toxin (e.g., the neurotoxic component of botulinum toxin, preferably of type A) at a concentration such as 10 to 150 U/ml, a salt (e.g., sodium chloride) in a concentration such as 0.5% to 1.5% w/v, a sugar (e.g., a mono- or disaccharide, such as glucose, fructose, galactose, trehalose, sucrose and maltose) at a concentration such as 0.1% to 2% w/v, and a stabilizing protein (e.g., albumin) at a concentration such as 0.001% to 4% w/v, 0.01% to 3% w/v, 0.1% to 1% w/v or, particularly, 0.01% to 0.5% or 0.01 to 0.5%.

Another preferred aqueous botulinum formulation for use herein essentially consists of water, botulinum toxin (e.g. the neurotoxic component of botulinum toxin type A), sodium chloride, sucrose, and albumin (e.g., human serum albumin; HSA). The concentration of the mentioned components may be in the following ranges: 10 to 200 U/ml or 30 to 125 U/ml (botulinum toxin), 0.5% to 1.5% w/v or 0.7% to 1.1% w/v (sodium chloride), 0.1% to 2% w/v or 0.2% to 1% w/v (sucrose), 0.01% to 1% w/v, 0.05% to 0.5% w/v, 0.1% to 3% w/v or 0.5% to 1.5% w/v (HSA). A further preferred botulinum toxin formulation for use herein is a Xeomin® solution, e.g., reconstituted with physiological saline (0.9% sodium chloride), including 20 to 150 U/ml of the neurotoxic component of botulinum toxin type A.

The term "essentially consists of", as used herein is intended to mean that substances other than those indicated are only contained in trace amounts, e.g. unavoidable impurities contained in the components used for formulating the liquid (aqueous) botulinum toxin formulation, and low amounts of impurities included in the isolated botulinum toxin (e.g., the neurotoxic component of botulinum toxin type A) as a result of the purification procedure (e.g., very low residual amounts of buffers, chelating agents and the like).

Preferably, the liquid botulinum toxin formulation in the botulinum toxin prefilled syringe system does not contain a buffer.

The present invention is further based on the surprising finding that a liquid botulinum toxin formulation in a glass syringe is stable after storage for a prolonged period of time at reduced temperature (e.g., 2-8° C.) and even at ambient temperature (e.g., 25° C.). The botulinum toxin prefilled syringe system of the present invention therefore advantageously exhibits an extended shelf life. Moreover, the high long-term stability provides tolerance against interruptions of the cool chain and may facilitate the approval procedure and/or the commercialization in all climate zones, including countries with hot climate.

Preferably, the toxin activity is not reduced by more than 25%, relative to the initial toxin activity, upon storage of the prefilled container for (a) 12 months at standard refrigerator temperature (i.e. 2-8° C., such as 5° C.) and (b) 12 months at 25° C. More preferably, the toxin activity is not reduced by more than 20% or 15%, relative to the initial toxin activity, upon storage of the prefilled syringe for (a) 6 months at 2-8° C. (e.g., 5° C.) or (b) 6 months at 25° C. Particularly preferable, the toxin activity is not reduced by more than 10%, relative to the initial toxin activity, upon storage of the prefilled syringe for (a) 3 to 6 months at 2-8° C. (e.g., 5° C.) or (b) 3 to 6 months at 25° C. Especially preferable, the toxin activity is not reduced by more than 5%, relative to the initial toxin activity, upon storage of the prefilled syringe for (a) 3 to 6 months at 2-8° C. (e.g., 5° C.) or (b) 3 to 6 months at 25° C.

Surprisingly, the liquid botulinum toxin formulation in the prefilled syringe is also stable for even longer storage times of up to 24 months or even longer. For example, upon storage for up to 24 months (e.g., 15, 18 or 24 months) at 2-8° C. (e.g., 5° C.) or 25° C., the toxin activity is preferably not reduced by more than 30% or 25%, more preferably by no more than 20%, in particular by no more than 15%, particularly preferable by no more than 10%, and most preferable by no more than 5%, relative to the initial toxin activity.

In particular, the toxin activity is preferably not reduced by more than 25%, 20%, 15%, 10% or 5%, relative to the initial toxin activity, upon storage of the prefilled syringe for 24 months at 2-8°. Upon storage of the prefilled syringe at 2-8° for 18 months, the toxin activity is preferably not reduced by more than 25%, 20%, 15%, 10% or 5%, relative to the initial toxin activity. Furthermore, the toxin activity is preferably not reduced by more than 35%, 30%, 25%, 20% or 15%, relative to the initial toxin activity, upon storage of the prefilled syringe for 24 months at 25° C. Upon storage of the prefilled syringe at 25° C. for 18 months, the toxin activity is preferably not reduced by more than 30%, 25%, 20%, 15% or 10%, relative to the initial toxin activity.

Within the present invention, the term "toxin activity" is intended to refer to the biological activity of the botulinum toxin. "Biological activity" may refer to (a) receptor binding, (b) internalization, (c) translocation across the endosomal membrane into the cytosol, and/or (d) endoproteolytic cleavage of proteins involved in synaptic vesicle membrane fusion. For example, any LC (light chain) domain, which shows proteolytic activity of more than 10%, 20%, 30%, 40%, 50%, 60%, 70%, 80%, 90% and up to 100% of the corresponding wild-type LC domain in a SNAP-25 assay may be considered "biological active" or "to exhibit proteolytic activity" within the scope of this invention. Furthermore, any HC (heavy chain) domain that is capable of binding to a cellular HC domain receptor, in particular to its native HC domain receptor, and is capable of translocating an LC domain attached to it, is considered "biologically active".

The biological activity is expressed in Mouse Units (MU). As used herein, 1 MU is the amount of neurotoxic component, which kills 50% of a specified mouse population after intraperitoneal injection, i.e. the mouse i.p. $LD_{50}$, as measured in accordance with the method of Schantz and Kauter (Schantz and Kauter, J. Assoc. Off. Anal. Chem. 1978, 61:96-99). The terms "MU" and "Unit" or "U" are used interchangeably herein.

Suitable assays for assessing the biological activity include the mouse hemidiaphragm assay (MHA) described by Pearce et al. (Toxicol. Appl. Pharmacol. 128:69-77, 1994), the hemidiaphragm assay (HDA) according to Göschel et al. (Experimental Neurology 147:96-102, 1997), the mouse diaphragm assay (MDA) according to Dressler et al. (Mov. Disord. 20:1617-1619, 2005), the SNAP-25 protease assay (e.g., the "GFP-SNAP25 fluorescence release assay" described in WO 2006/020748 or the "improved SNAP25 endopeptidase immuno-assay" described in Jones et al., 2008, J. Immunol. Methods 329:92-101), the electrochemoluminescence (ECL) sandwich ELISA described in WO 2009/114748, and cell-based assays as those described in WO 2009/114748, WO 2004/029576, WO 2013/049508 and, in particular, WO 2014/207109.

As used herein, the term "initial toxin activity" or "initial potency" generally refers to the activity of the botulinum toxin at the beginning of the measurement (t=0). Typically, t=0 is shortly after preparation of the toxin. Further, the term "upon storage", as used herein is intended to mean after storage for a certain time period. In addition, the term "during storage" generally means over the course of the entire storage period.

Furthermore, the number of subvisible particles of equal to or greater than 10 µm is below 1000/ml during storage for 6 to 24 months at 2° C. to 30° C. In addition, the pH value typically is not increased or decreased by more than 10%, relative to the initial pH value, upon storage of the prefilled syringe for 6 to 12 months at 5° C. or 25° C.

In addition, the liquid botulinum toxin formulation is highly stable in terms of the subvisible particle count. A "subvisible particle" within the meaning of the present invention is typically a particle with a diameter below 100 µm. Specifically, the count (or number) of particles equal to or greater than 10 µm in the liquid botulinum toxin formulation is typically below 1000/ml, preferably below 600/ml and more preferably below 200/ml during storage for 6 to 24 months (e.g., 6, 9, 12, 15, 18 or 24 months) at 2-30° C. (e.g., at 5° C., 25° C. or 30° C.).

Particle measurements may be conducted by different methods, such as Micro-Flow Imaging (MFI), Resonant Mass Measurement (RMM), and Nanoparticle Tracking Analysis (NTA). The particle measurements usually follow USP <788>. Within the context of the present invention, the Micro-Flow Imaging measurement is preferably used. This measurement method may, for example, be conducted using a DPA-5200 particle analyzer system (ProteinSimple, Santa Clara, Calif., USA) equipped with a silane coated high-resolution 100 µm flow cell. Generally, the samples are analyzed undiluted. Alternatively, Resonant Mass Measurements (RMM) may be employed to determine the number of particles using, for example, the ARCHIMEDES Particle Metrology System (Affinity Biosensors, Santa Barbara, Calif., USA).

Moreover, the liquid botulinum toxin formulation shows high pH stability in that the pH value is essentially stable during storage of the prefilled syringe. Preferably, the pH value is not increased or decreased by more than 15%, 10%, 8% or 6%, relative to the initial pH value, upon storage of the prefilled syringe for 6 to 24 months (e.g., 6, 9, 12, 15, 18 or 24 months) at 2-30° C. (e.g., at 5° C., 25° C. or 30° C.), for example for 18 months at 25° C. or for 24 months at 25° C. The pH may be measured in accordance with the US Pharmacopeia standardized test method USP <791>, which outlines pH measurements for a multitude of pharmaceutical product. Any suitable pH meter may be used, for example the Lab 870 pH meter of Schott Instruments.

It is also contemplated that, in a specific aspect, the present invention relates to a botulinum toxin prefilled syringe system as described herein with the proviso that it is not a botulinum toxin prefilled syringe system having (a) a syringe barrel, a tip cap and a plunger stopper made of the materials disclosed in Table 1 of International application No. PCT/EP2015/002602 or, alternatively, in Table 1 herein below in the Examples sections, and optionally (b) a syringe size and/or type disclosed in Table 1 of International application No. PCT/EP2015/002602 or, alternatively, in Table 1 herein below in the Examples sections. Further, the botulinum toxin prefilled syringe system of the present invention may not be one of the botulinum toxin prefilled syringe configurations A, B, G and H disclosed in Table 1 of International application No. PCT/EP2015/002602 or, alternatively, in Table 1 herein below.

In view of the above, the botulinum toxin prefilled syringe system of the present invention is particularly suitable for applications, including cosmetic and therapeutic application, requiring administration of the toxin in multiple injections (e.g., 2 to 8, 3 to 6 or 4 to 5 injections) and, optionally, low amounts of toxin, in which case precise and accurate injection is of particular importance. This is, the botulinum toxin prefilled syringe system of the present invention may be used for multiple injections (i.e. 2 to 8, or 3 to 6, or 4 to 5 injections).

For example, in cosmetic applications or treatments (e.g., in the treatment of glabellar frown lines, horizontal forehead lines, crow's feet, etc.), multiple injection sites (e.g., 2 to 8 or 3 to 6) may be injected using the prefilled syringe system of the present invention. Typically, the amount of toxin administered per injection site is small (e.g., 1 to 10 U or 2 to 5 U). In case of therapeutic applications (e.g., spasm, Torticollis spasmodicus, blepharospasm, etc.), the number of injections may be, e.g., 2 to 5. The dose applied per injection site is usually much higher than for cosmetic applications (e.g., 30 to 200 U or 50 to 100 U).

In a second aspect, the present invention provides a kit comprising a botulinum toxin prefilled syringe system according to the first aspect of the present invention and optionally instructions for use of said botulinum toxin prefilled syringe system.

In a third aspect, the present invention provides a botulinum toxin prefilled syringe system according to the first aspect of the invention for use in therapy. Preferably, the botulinum toxin prefilled syringe system is used for treating a disease or condition caused by or associated with hyperactive cholinergic innervation of muscles or exocrine glands in a patient including, but not limited to, dystonia, spasticity, paratonia, diskinesia, focal spasm, strabismus, tremor, tics, migraine, sialorrhea and hyperhidrosis.

The term "hyperactive cholinergic innervation", as used herein, relates to a synapse, which is characterized by an unusually high amount of acetylcholine release into the synaptic cleft. "Unusually high" relates to an increase of, e.g., up to 25%, up to 50% or more with respect to a reference activity which may be obtained, for example, by comparing the release with the release at a synapse of the same type but which is not in a hyperactive state, wherein muscle dystonia may be indicative of the hyperactive state.

"Up to 25%" means, for example, about 1% to about 25%. Methods for performing the required measurements are known in the art.

Within the present invention, the disease or condition caused by or associated with hyperactive cholinergic innervation of muscles includes, but is not limited to, dystonias (e.g., blepharospasm, spasmodic torticollis, limb dystonia, and task-specifc dystonias such as writer's cramps), spasticities (e.g., post-stroke spasticity, spasticity caused by cerebral palsy), paratonia, diskinesias (e.g., tardive diskinesia) focal spasms (e.g., hemifacial spasm), (juvenile) cerebral palsy (e.g., spastic, dyskinetic or ataxic cerebral palsy), strabismus, pain (e.g. neuropathic pain), wound healing, tremors, tics, and migraine.

The botulinum toxin prefilled syringe of the present invention is particularly useful in the treatment of dystonia of a muscle. Exemplary dystonias include, but are not limited to, dystonias selected from the group consisting of (1) cranial dystonia, including blepharospasm and oromandibular dystonia of the jaw opening or jaw closing type, (2) cervical dystonia, including antecollis, retrocollis, laterocollis and torticollis, (3) pharyngeal dystonia, (4) laryngeal dystonia, including spasmodic dysphonia, (5) limb dystonia, including arm dystonia such as task specific dystonias (e.g., writer's cramp), leg dystonia, axial dystonia, segmental dystonia, and (6) other dystonias.

The "hyperactive exocrine gland" to be treated within the context of the present invention is not particularly limited and covers any exocrine gland with hyperactivity. It is therefore envisaged that the present invention can be applied to the treatment involving any of the glands mentioned in Sobotta, Johannes, Atlas der Anatomie des Menschen. 22. Auflage. Band 1 and 2, Urban & Fischer, 2005, which is incorporated herein by reference. Preferably, the hyperactive gland is an autonomic exocrine gland. The botulinum toxin composition is preferably injected into or in the vicinity of the hyperactive exocrine gland.

Within the present invention, the hyperactive exocrine gland may be selected from the group consisting of sweat gland, tear gland, salivary gland and mucosal gland. Alternatively, the hyperactive gland may also be may be associated with a disease or condition selected from the group consisting of Frey syndrome, Crocodile Tears syndrome, axillar hyperhidrosis, palmar hyperhidrosis, plantar hyperhidrosis, hyperhidrosis of the head and neck, hyperhidrosis of the body, rhinorrhea, or relative hypersalivation in patients with stroke, Parkinson's disease or amyotrophic lateral sclerosis. In particular, the disease or condition caused by or associated with hyperactive cholinergic innervation of exocrine glands may include drooling (hypersalivation, sialorrhea) and excessive sweating (hyperhidrosis).

The administration is not limited to any particular administration regimen, mode, form, dose and interval. As known to those skilled in the art, the administered amount or dose of botulinum toxin depends on the mode of application, the type of disease, the patient's weight, age, sex and state of health, and which target tissues are chosen for injection. The botulinum toxin formulation is usually administered locally, e.g., by subcutaneous or intramuscular injection into or in the vicinity of the target tissues (e.g., muscles, skin, exocrine glands).

Furthermore, different muscles, depending on their size, generally require different dosing. A suitable dose may range from 10 to 2000 U, preferably from 50 to 500 U, and more preferably from 100 to 350 U of botulinum toxin. For the treatment of exocrine glands, the dose is usually in the range of 10 to 500 U, preferably 20 to 200 U, and more preferably 30 to 100 U. Such total amounts may be administered on the same day or on a subsequent day of treatment. For example, during a first treatment session a first fraction of the dose may be administered. During one or more treatment sessions, the remaining fraction of the total dose may be administered. Further, the frequency of application is not particularly limited and suitable administration intervals may be three months or less (e.g., 4 or 8 weeks) or more than three months.

In a fourth aspect, the present invention relates to the use of the botulinum toxin prefilled syringe according to the first aspect of the invention in cosmetic applications, such as for treating facial asymmetries and wrinkles and lines of the skin (e.g., facial lines and facial wrinkles), such as upper facial rhytides, platysma bands, glabellar frown lines, nasolabial folds, chin folds, marionette lines, buccal commissures, perioral wrinkles, crow's feet, and jawlines.

The amounts of botulinum toxin administered for cosmetic application are usually in the range of 1 to 100 U, 5 to 10 U, 10 to 20 U or 20 to 50 U. Such total amounts may be administered on the same day or on a subsequent day of treatment. For example, during a first treatment session a first fraction of the dose may be administered. This first fraction is preferably a suboptimal fraction, i.e. a fraction, which does not remove the wrinkles or skin lines completely. During one or more treatment sessions, the remaining fraction of the total dose may be administered.

In a fifth aspect, the present invention provides a method for treating a disease or condition caused by or associated with hyperactive cholinergic innervation of muscles or exocrine glands in a patient, the method comprising locally administering an effective amount of botulinum toxin to a muscle or exocrine gland of the patient using the botulinum toxin prefilled syringe system according to the first aspect of the invention.

The term "effective amount", as used herein, refers to the amount of a botulinum toxin sufficient to effect beneficial or desired therapeutic, cosmetic or anesthetic result. In the present context, the term "local administration" within the meaning of the present invention refers preferably to subcutaneous or intramuscular injection into or in the vicinity of the target tissues (e.g., muscles, skin, exocrine glands). The term "patient", as used herein, generally relates to a human afflicted with a disease or condition caused by or associated with hyperactive cholinergic innervation of muscles or exocrine glands in a patient, or to a human in need of a cosmetic or anesthetic treatment. As used herein, "patient" may be interchangeably used with "subject" or "individual".

The administration is not limited to any particular administration regimen, mode, form, dose and interval. As used herein, the term "to the muscle or exocrine gland" means that the botulinum toxin may be administered into, or in vicinity of, one or more muscles or exocrine glands. Usually, the botulinum toxin is administered by local intramuscular injection. With respect to further details regarding the administration (e.g., regimen, mode, form, dose and interval) and the disease or conditions to be treated, the same comments apply as those set out above in relation to the use of the prefilled glass container (e.g. prefilled botulinum toxin syringe) for cosmetic and therapeutic applications.

In a sixth aspect, the present invention provides a method for the cosmetic treatment of the skin, particularly for treating wrinkles of the skin and facial asymmetries, the method comprising locally administering an effective amount of botulinum toxin to a patient by injection, e.g., intradermal, subdermal or subcutaneous injection, using the botulinum toxin prefilled syringe system according to the first aspect of the present invention. Since this aspect is closely related to other aspects of the present invention described above, all comments, definitions and explanations given above in relation to these other aspects equally apply rto the sixth aspect, unless otherwise stated.

The present invention will now be further illustrated by the following, non-limiting examples.

Examples

The following examples illustrate the present invention by several embodiments of the botulinum toxin prefilled syringe system of the present invention (in the following referred to as "configurations A, B, G, and H"), and show that the botulinum toxin prefilled syringe system of the present invention is stable and has enhanced functionality in terms of injection characteristics, even after long-term storage and at elevated temperatures.

Materials & Methods

Materials

In order to evaluate the performance of different botulinum toxin prefilled syringe systems according to the present invention, the following aqueous botulinum toxin solution was used: incobotulinumtoxinA (50 U/ml), 1.0 mg/ml human albumin, 4.7 mg/ml sucrose, 0.9% saline (reconstituted Xeomin®). Luer-Lock glass syringes of four different configurations (A, B, G and H; see Table 1) where each filled with 1 ml of the botulinum toxin solution and closed by inserting a plunger into the proximal end of the syringe barrel. The resulting prefilled syringes were then stored at standard refrigerator temperature (2-8° C.) or 25° C. for predetermined periods of time.

load cell and Emperor force software. A 32 G×½" test needle (Steriject PRE-32013, TSK Laboratory, Japan) was fitted to the syringe tip for the force measurements. Testing was carried out at room temperature (about 20° C.) and at a displacement speed of 100 mm/min into air. All measurements were performed using the filled syringes, i.e. no "empty syringe measurements" were carried out.

The force required for gliding the plunger stopper and plunger were recorded and presented as force versus displacement plots. Each force measurement was performed several times using a number of identically prepared and stored prefilled syringes to take into account the variability of single measurements.

The following parameters were determined from the force vs. displacement plots:
  maximum gliding force ($GF_{max}$): the measured highest gliding force in Newtons (N) before the plunger stopper finishes its course at the distal end of the syringe barrel,
  break loose force (BLF): the highest force between 0 and 2 mm plunger displacement distance, and
  dynamic gliding force (DGF): the mean gliding force calculated from the measured gliding forces at ⅓ and ⅔ of the total plunger displacement distance in N.

Toxin Stability Measurement

The stability of the botulinum toxin solution was determined without storage ("fresh"; storage time=0 months) and after storage for 1, 3, 6, 9, 12, and 18 months at predetermined temperatures by measuring the remaining toxin potency.

The toxin potency was determined by a hemidiaphragm assay. The assay is conducted using a murine nerve muscle preparation which is maintained in an organ bath containing

TABLE 1

Syringe configurations A, B, G, and H

| CONF. | COMP. | SYRINGE BARREL | | TIP CAP | | PLUNGER STOPPER | |
|---|---|---|---|---|---|---|---|
| | | Product name | Material | Product name | Material | Product Name | Material |
| A | Gerresheimer | RTF ® 1.0 mL long Luer Lock syringe with TELC (tamper evident Luer Lock Closure) | Borosilicate glass of type 1; inner surface of glass barrel is siliconized by "Baked on Siliconization"[1]; sterilized by EtO | Helvoet ® FM 27 Grey[1] (=Datwyler FM 27/0) | Styrene-butadiene rubber compound (without MBT(2-mercaptobenzothiazole)) | West ® 4023/50, grey rubber, FluroTec ® coated | Bromobutyl elastomer (reinforced with inert mineral), coated with FluroTec ® film |
| B | Gerresheimer | see A | see A | see A | see A | West ® 4023/50G NovaPure ® | Elastomer formulation (bromo butyl), coated with FluroTec ® film |
| G | Becton Dickinson | BD Hypak SCF ™ 1 ml PRTC (plastic rigid tip cap) | Borosilicate type I glass; inner surface of glass barrel is spray-siliconized using a silicone oil; sterilized by EtO | PRTC FM 27 Grey | Styrene-butadiene rubber compound (free from MBT) | BD Hypak ™ BSCF 4023/50 grey FluroTec ® (West ®) | Bromobutyl elastomer reinforced with an inert mineral and coated with a FluroTec ® film |
| H | Becton Dickinson | see G | see G | PRTC 7025/65 grey (West ®) | Synthetic isoprene-bromobutyl blend (reinforced with an inert mineral) | see G | see G |

[1]Siliconized with Dow Corning 365, Dimethicone NF emulsion, followed by a thermal fixation process
2 = BSCF (bagged sterile, clean and ready-to fill; utilizes bagged (BSCF) stoppers)

Gliding Force Measurement

Gliding and break loose force were measured using a Mecmesin Multitest 2.5-xt force testing system (Mecmesin GmbH, Germany) combined with a Mecmesin ILC 100N 4 ml of medium. The muscle is attached to a force transducer and electrically stimulated via the phrenic nerve resulting in a isometric contraction force which remains constant for more than 180 min if no toxin is added.

Upon introduction of toxin to the organ bath, the contraction amplitude of the nerve-stimulated muscle gradually declines. The contraction amplitude of the diaphragm is monitored over time. As a read-out, the time at which half the initial contraction force is reached is determined and referred to as paralysis time. The paralysis time is proportional to the amount of active toxin present.

Particle and pH Measurement

Particle measurements were conducted using Micro-Flow Imaging. The Micro-Flow Imaging measurements were conducted using a DPA-5200 particle analyzer system (ProteinSimple, Santa Clara, Calif., USA) equipped with a silane coated high-resolution 100 μm flow cell. The samples were analyzed undiluted. MFI View System Software (MVSS) version 2-R2-6.1.20.1915 was used to perform the measurements, and MFI View Analysis Suite (MVAS) software version 1.3.0.1007 was used to analyze the samples.

The pH measurements were performed in accordance with the US Pharmacopeia standardized test method USP <791>, which outlines pH measurements for a multitude of pharmaceutical product, using a pH meter (Lab 870, Schott Instruments).

Results

Figure 3:
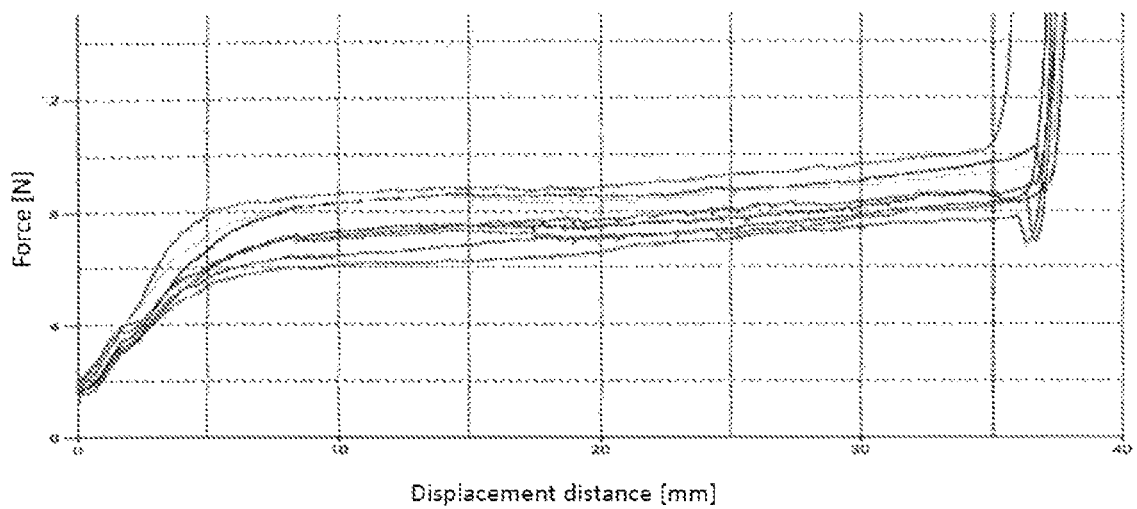
FIG. 3 is a gliding force versus plunger displacement plot for an exemplary botulinum toxin prefilled syringe with 1 ml filling volume (configuration B), as measured via a 32 G×½" needle at 20° C. and applying a displacement speed of 100 mm/min, wherein the curves shown correspond to several individual syringes measured.

A typical force vs. displacement plot obtained for the prefilled syringes tested is shown in FIG. 3. Each single curve shown in FIG. 3 represents a single measurement of a prefilled syringe of configuration B after storage for 4 weeks at 25° C. As can be seen, there are three different parts in the force vs. displacement plot: a first increase of force due to the initial gliding force required to initiate plunger movement, a second plateau-like part, and a third rapid increase of force due to the compression of the plunger against the end of the syringe barrel.

The parameters of injectability for syringe configuration B after storage for 0, 12 and 24 months at 2-8° C. and 25° C., as determined from the force vs. displacement plots, are shown in Table 2.

TABLE 2

Maximum gliding force ($GF_{max}$), maximum break loose force (BLF), and dynamic gliding force (DGF) for syringe configuration B.

| | | STORAGE TIME | | |
|---|---|---|---|---|
| FORCE | TEMP. | 0 months (fresh) [N] | 12 months [N] | 24 months [N] |
| $GF_{max}$ | 2-8° C. | 10 | 11 | 11 |
| | 25° C. | 10 | 11 | 12 |
| BLF | 2-8° C. | 2 | 3 | 3 |
| | 25° C. | 2 | 5 | 5 |
| DGF | 2-8° C. | 9 | 9 | 9 |
| | 25° C. | 9 | 10 | 10 |

The maximum gliding force ($GF_{max}$) and maximum break loose force (BLF) of all syringe configurations studied (i.e. A, B, G, and H) upon long-time storage for 24 months at standard refrigerator temperature (2-8° C.) and at 25° C. are summarized in Table 3.

TABLE 3

Comparison of maximum gliding force ($GF_{max}$) and maximum break loose force (BLF) of syringe configurations A, B, G, and H stored for 24 months at 2-8° C. and 25° C.

| | | CONFIGURATION | | | |
|---|---|---|---|---|---|
| FORCE | TEMP. | A | B | G | H |
| $GF_{max}$ | 2-8° C. | 17 | 11 | 9 | 6 |
| | 25° C. | 20 | 12 | 9 | 8 |
| BLF | 2-8° C. | 5 | 3 | 4 | 4 |
| | 25° C. | 3 | 5 | 5 | 5 |

The results of the stability measurements for configurations A, B, G, and H are shown in Table 4 below.

TABLE 4

Stability in terms of potency

| | | STABILITY (toxin potency in %, relative to the initial toxin activity) | | | | | | |
|---|---|---|---|---|---|---|---|---|
| | | | Time (months) | | | | | |
| CONFIG. | Temperature | t = 0 (initial)* | 1 | 3 | 6 | 9 | 12 | 18 |
| A | 2-8° C. | 100 | 102 | 102 | 100 | 107 | 109 | 88 |
| B | | 100 | 109 | 96 | 102 | 102 | 96 | 109 |
| G | | 100 | 100 | 100 | 96 | 91 | 102 | 96 |
| H | | 100 | 100 | 114 | 102 | 112 | 100 | 108 |
| A | 25° C. | 100 | 98 | 102 | 107 | 93 | 89 | 73 |
| B | | 100 | 102 | 100 | 107 | 94 | 107 | 87 |
| G | | 100 | 93 | 104 | 96 | 98 | 98 | 75 |
| H | | 100 | 108 | 116 | 100 | 90 | 80 | 73 |

*The initial absolute toxin activity in units ranges from 51 U to 56 U

Figure 4:
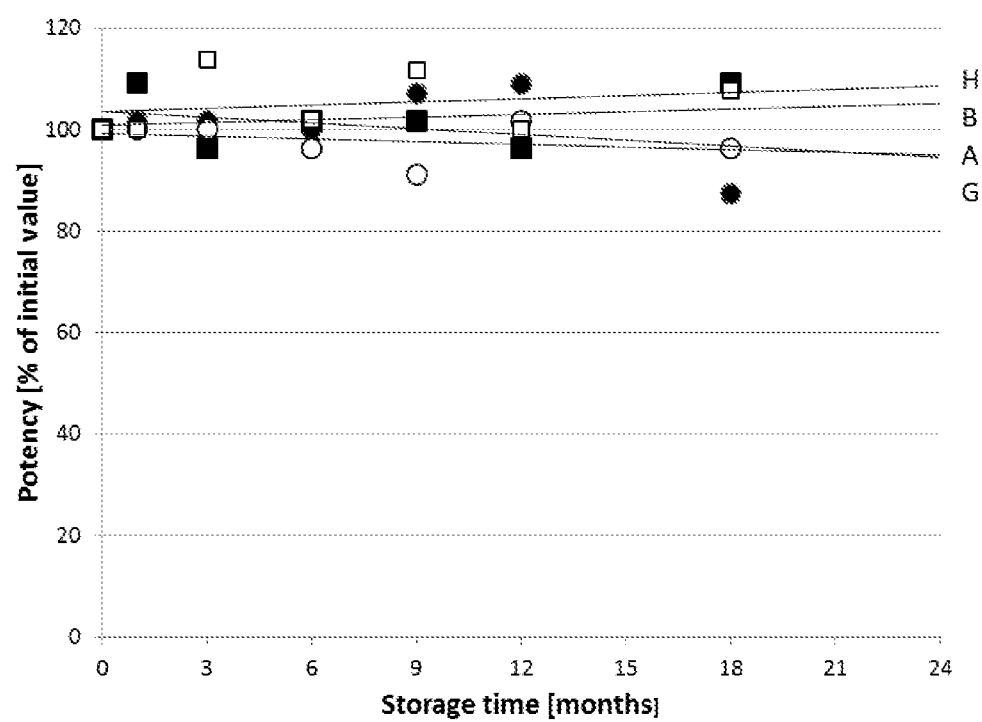
FIG. 4 is a graph showing the stability of a liquid botulinum toxin formulation in prefilled syringe configurations A, B, G, and H at 2-8° C. as a function of time (configuration A: (●), configuration B: (■), configuration H: (□), and configuration G: (○))
Figure 5:
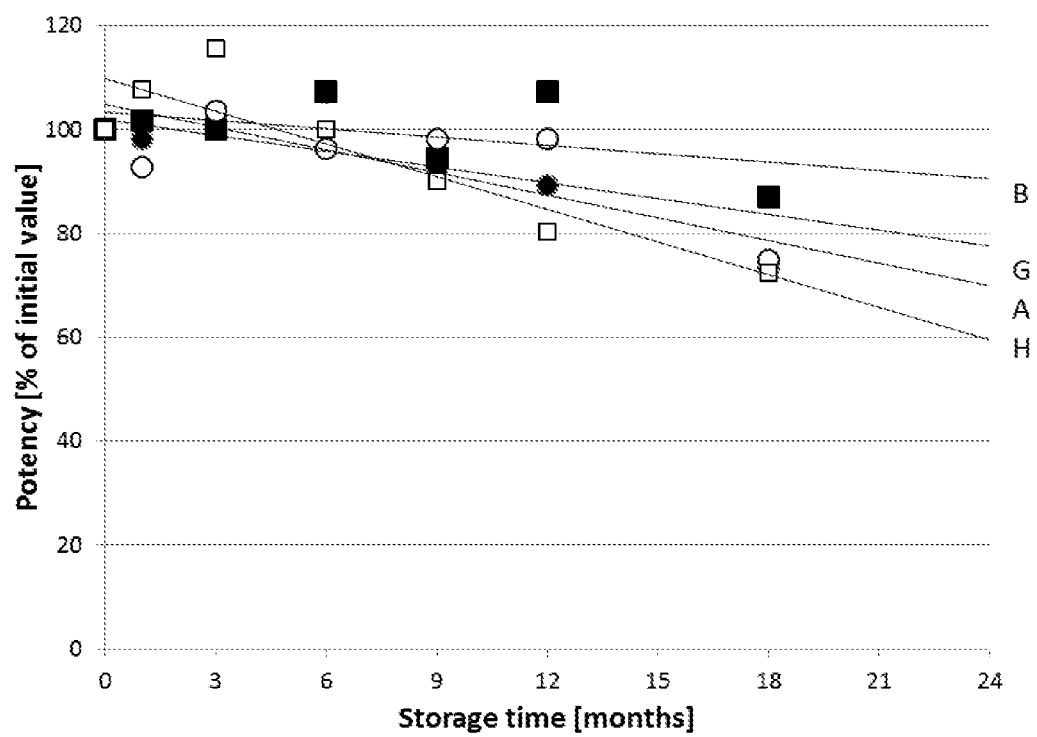
FIG. 5 is a graph showing the stability of a liquid botulinum toxin formulation in prefilled syringe configurations A, B, G, and H at 25° C. as a function of time (configuration A: (●), configuration B: (■), configuration H: (□), and configuration G: (○)).

The above stability data are graphically shown in FIG. 4 (stability at 2-8° C.) and FIG. 5 (stability at 25° C.). The potency values at 24 months can be estimated from an extrapolation to 24 months of storage.

As can be seen from Table 4 and FIGS. 4 and 5, the maximum measured loss of biological activity is only 12% and 20% for the temperature conditions 2-8° C. (up to 18 months) and 25° C. (up to 12 months), respectively. The loss in biological activity after storage for 24 months at 2-8° C. is estimated to be less than 5% for all configurations A, B, G, and H, and for syringe configuration B the stability loss after storage for 24 months at elevated temperature of 25° C. is still excellent and estimated to be less than 10%.

The pH measurements up to 18 months revealed that the pH remained exceptionally stable over a period of up to 18 months. No trend towards higher or lower values was observed and all measured pH values remained within ±0.5 of the initial pH (results not shown). Moreover, particle size measurements by Micro-Flow Imaging showed no significant increase in the particle count upon storage for up to 18 months at 2-8° C. and 25° C., and remained well below 1000/ml (results not shown).

In conclusion, the results demonstrate that the botulinum toxin prefilled syringe system of the present invention exhibits excellent functionality as mirrored by low gliding and break loose forces over the entire shelf-life of up to 24 months. Also, the liquid botulinum toxin formulation in the prefilled syringe system have been shown to be stable for up to 24 months at 2-8° C., and to be stable even at an elevated temperature of 25° C. for no less than about 9 to 12 months. Therefore, the botulinum toxin prefilled syringe system of the present invention has a great potential and represents a significant contribution to the safe, convenient and reliable management of a wide variety of botulinum toxin-treated therapeutic and cosmetic indications.

The invention claimed is:

1. A botulinum toxin prefilled syringe system comprising:
a syringe barrel of glass, the syringe barrel including an inner surface defining a chamber containing a liquid botulinum toxin formulation, having a proximal end and a distal end, and having a label attached to an outside surface of the syringe barrel;
a plunger stopper slidably positioned inside the syringe barrel and providing a fluid-tight seal of the proximal end of the syringe barrel;
a closure device attached to the distal end of the syringe barrel, the closure device having an outlet engaging portion sealingly engaging and closing a distal open outlet end of the syringe system to prevent leakage of the liquid botulinum toxin formulation;
wherein the plunger stopper has a plurality of annular ribs providing multiple discrete contact areas to engage with the inner surface of the syringe barrel, wherein the plurality of annular ribs of the plunger stopper is three to five annular ribs, and
wherein the botulinum toxin prefilled syringe system has a normalized maximum gliding force of 15 N or less, as measured at a temperature of 20° C. and using a 32 G×½" needle and a displacement speed of 100 mm/min, wherein the normalized maximum gliding force is defined as follows:

$$GF_{max} = GF_{measured} \times (d_{barrel})^2 / (D_{barrel})^2$$

wherein:
$GF_{max}$ is the normalized maximal gliding force in N,
$GF_{measured}$ is the measured highest gliding force in N before the plunger stopper finishes its course at the distal end of the syringe barrel,
$d_{barrel}$ is the barrel inner diameter of a reference syringe and is 6.35 mm, and
$D_{barrel}$ is the inner barrel diameter in mm of the prefilled syringe system, and
the botulinum toxin prefilled syringe system has a normalized break loose force of 8 N or less, as measured at a temperature of 20° C. using a 32 G×½" needle and a displacement speed of 100 mm/min, wherein the normalized break loose force is defined as follows:

$$BLF_{norm} = BLF_{measured} \times (d_{barrel})^2 / (D_{barrel})^2$$

wherein:
$BLF_{norm}$ is the normalized break loose force in N,
$BLF_{measured}$ is the measured break loose force in N and is defined as the highest force between 0 and 2 mm plunger displacement distance,
$d_{barrel}$ is the barrel inner diameter of a reference syringe and is 6.35 mm, and
$D_{barrel}$ is the inner barrel diameter in mm of the prefilled syringe system, wherein the multiple discrete contact areas each provide an independent seal with the inner surface of the syringe barrel,
wherein the annular ribs extend outward radially from an axis of the plunger stopper,
wherein the annular rib located adjacent to the distal end of the plunger stopper has a greater Full Width at Half Maximum (FWHM) than the other annular ribs of the plunger stopper, wherein the FWHM is the width in an axial direction of the plunger stopper between two points on the surface of an annular rib, wherein the two points are located at half the maximum height of the annular rib in a perpendicular direction to the axis of the plunger stopper, and
wherein the distance between any two proximal adjacent annular ribs, except the most distal annular rib, in the axial direction of the plunger stopper is more than two times the sum of the full width at half maximum (FWHM) of the two proximal adjacent annular ribs.

2. The botulinum toxin prefilled syringe system of claim 1, wherein a normalized break loose force is 6 N or less, as measured at a temperature of 20° C. using a 32 G×½" needle and a displacement speed of 100 mm/min.

3. The botulinum toxin prefilled syringe system of claim 1, wherein a normalized dynamic gliding force is 15 N or less, as measured at a temperature of 20° C. using a 32 G×½" needle and a displacement speed of 100 mm/min, wherein the normalized dynamic gliding force is defined as follows:

$$DGF_{norm} = DGF_{measured} \times (d_{barrel})^2 / (D_{barrel})^2$$

wherein:
$DGF_{norm}$ is the normalized dynamic gliding force in N,
$DGF_{measured}$ is the mean gliding force calculated from the measured gliding forces at ⅓ and ⅔ of the total plunger displacement distance in N,
$d_{barrel}$ is the barrel inner diameter of a reference syringe and is 6.35 mm, and
$D_{barrel}$ is the inner barrel diameter in mm of the prefilled syringe system.

4. The botulinum toxin prefilled syringe system of claim 3, wherein the normalized dynamic gliding force is 15 N or less after storage of the botulinum toxin prefilled syringe system for 12 to 24 months at 2 to 8° C. or for 12 to 24 months at 25° C., as measured at a temperature of 20° C. using a 32 G×½" needle and a displacement speed of 100 mm/min.

5. The botulinum toxin prefilled syringe system of claim 1, wherein
(i) the plunger stopper has a normalized total contact area with the inner surface of the syringe barrel of 70 mm² or less, wherein the normalized total contact area is calculated as follows:

$$TCA_{norm} = TCA_{calc} \times (d_{barrel})^2 / (D_{barrel})^2$$

wherein:
$TCA_{norm}$ is the normalized total contact area in mm²,
$TCA_{calc}$ is the calculated total contact area in mm² and is defined as the sum of the contact surfaces ($CT_{rib}$) of each annular rib in mm², wherein $CT_{rib} = 2\pi rh$, with r being the greatest distance perpendicular to the axis of the plunger stopper between a point on the surface of the annular rib and the axis of the plunger stopper in mm, and h being the full width at half maximum (FWHM) of the annular rib in mm, the FWHM being defined as the width in the axial direction of the plunger stopper between those two points on the surface of the annular rib which are half the maximum height of the annular rib in perpendicular direction to the axis of the plunger stopper,
$d_{barrel}$ is the barrel inner diameter of a reference syringe and is 6.35 mm, and
$D_{barrel}$ is the inner barrel diameter in mm of the prefilled syringe system, and/or
(ii) the percentage of the calculated total contact area of the plunger stopper with the inner surface of the syringe barrel relative to the total side face area of the plunger stopper is 50% or less, wherein the calculated total contact area (TCA$_{calc}$) is defined as in (i) and the total side face area of the plunger stopper is defined as follows:

$$TSFA=2\pi r_{max}H$$

wherein:

TSFA is the total side face area of the plunger stopper in mm$^2$, $r_{max}$ is the greatest distance perpendicular to the axis of the plunger stopper between a point on the surface of any annular rib and the axis of the plunger stopper in mm, and H is the total length of the plunger stopper in axial direction in mm.

6. The botulinum toxin prefilled syringe system of claim 1, wherein the inner surface of the syringe barrel is siliconized.

7. The botulinum toxin prefilled syringe system of claim 1, wherein the plunger stopper is of an elastomeric material.

8. The botulinum toxin prefilled syringe system of claim 7, wherein
   (i) the elastomeric material is a synthetic rubber selected from the group consisting of isoprene rubber, neoprene rubber, butadiene rubber, butyl rubber, styrene-butadiene copolymer, acrylonitrile-butadiene copolymer, polysulfide elastomers, urethane rubbers, and ethylene-propylene elastomers, or
   (ii) the plunger stopper further has a coating on at least a portion of the plunger stopper such that the liquid botulinum toxin formulation contacts only said coating during storage and/or injection, and the coating on at least a portion of the plunger stopper is a fluoropolymer coating, a crosslinked silicone coating, or a coating consisting of an outer crosslinked silicone coating layered on a fluoropolymer coating, or
   (iii) the elastomeric material is defined as in (i) and the coating is defined as in (ii).

9. The botulinum toxin prefilled syringe system of claim 7, wherein the elastomeric material is a halogenated butyl rubber.

10. The botulinum toxin prefilled syringe system of claim 1, wherein the outlet engaging portion of the closure device is of an elastomeric material.

11. The botulinum toxin prefilled syringe system of claim 10, wherein
    (i) the elastomeric material is a synthetic rubber selected from the group consisting of isoprene rubber, neoprene rubber, butadiene rubber, butyl rubber, styrene-butadiene copolymer, acrylonitrile-butadiene copolymer, polysulfide elastomers, urethane rubbers, and ethylene-propylene elastomers, or
    (ii) the outlet engaging portion of the closure device further has a coating on an outer surface thereof such that the liquid botulinum toxin formulation contacts only said coating during storage and/or injection, and the coating is a fluoropolymer coating, a crosslinked silicone coating, or a coating consisting of an outer crosslinked silicone coating layered on a fluoropolymer coating, or
    (iii) the elastomeric material is defined as in (i) and the coating is defined as in (ii).

12. The botulinum toxin prefilled syringe system of claim 10, wherein the elastomeric material is a styrene-butadiene copolymer, a butyl rubber, a halogenated butyl rubber, or a butyl rubber-isoprene rubber blend.

13. The botulinum toxin prefilled syringe system of claim 1, wherein botulinum toxin activity is not reduced by more than 25%, relative to an initial botulinum toxin activity, upon storage of the botulinum toxin prefilled syringe system for 12 months at 5° C. or 25° C.

14. A kit comprising the botulinum toxin prefilled syringe system according to claim 1.

15. The botulinum toxin prefilled syringe system of claim 1, wherein the plurality of annular ribs of the plunger stopper is three to four.

16. The botulinum toxin prefilled syringe system of claim 1, wherein the inner surface of the syringe barrel is spray-siliconized or baked-on siliconized.

17. The botulinum toxin prefilled syringe system of claim 1, wherein the normalized maximum gliding force is 12 N or less, as measured at a temperature of 20° C. using a 32 G×½" needle and a displacement speed of 100 mm/min.

18. The botulinum toxin prefilled syringe system of claim 1, wherein the normalized maximum gliding force is 8 N or less, as measured at a temperature of 20° C. using a 32 G×½" needle and a displacement speed of 100 mm/min.

19. The botulinum toxin prefilled syringe system of claim 1, wherein the normalized break loose force is 5 N or less, as measured at a temperature of 20° C. using a 32 G×½" needle and a displacement speed of 100 mm/min.

20. The botulinum toxin prefilled syringe system of claim 1, wherein
    the normalized maximum gliding force is 15 N or less after storage of the botulinum toxin prefilled syringe system for 12 to 24 months at 2 to 8° C. or for 12 to 24 months at 25° C., as measured at a temperature of 20° C. using a 32 G×½" needle and a displacement speed of 100 mm/min, and
    the normalized break loose force is 8 N or less after storage of the botulinum toxin prefilled syringe system for 12 to 24 months at 2 to 8° C. or for 12 to 24 months at 25° C., as measured at a temperature of 20° C. using a 32 G×½" needle and a displacement speed of 100 mm/min.

* * * * *